United States Patent [19]
Yokoyama

[11] Patent Number: 5,206,598
[45] Date of Patent: Apr. 27, 1993

[54] ISOTHERMAL CAPACITANCE TRANSIENT SPECTROSCOPY METHOD AND APPARATUS
[75] Inventor: Issei Yokoyama, Kyoto, Japan
[73] Assignee: Horiba, Ltd., Kyoto, Japan
[21] Appl. No.: 889,476
[22] Filed: May 27, 1992
[30] Foreign Application Priority Data
  Jun. 1, 1991 [JP] Japan .................. 3-157569
[51] Int. Cl.$^5$ ............................................. G01R 31/26
[52] U.S. Cl. .............................. 324/676; 324/158 D; 437/8
[58] Field of Search ................... 324/676, 678, 158 D, 324/158 T; 437/8; 427/8, 9, 10

[56] References Cited
U.S. PATENT DOCUMENTS

| Re. 32,457 | 7/1987 | Matey | 369/58 |
| 3,462,685 | 8/1969 | Hornak | 324/158 D |
| 3,665,307 | 5/1972 | Cocca | 324/158 T |
| 4,325,025 | 4/1982 | Corcoran et al. | 324/158 T |
| 4,509,012 | 4/1985 | Lin | 324/158 T |
| 4,839,588 | 6/1989 | Jantsch et al. | 324/158 D |

FOREIGN PATENT DOCUMENTS

3832298A1  9/1988  Fed. Rep. of Germany .
62-059852  3/1987  Japan .

OTHER PUBLICATIONS

Transient Spectroscopy of Deep Levels in Thin Semiconductor Films, K. Ng et al., Journal of Applied Physics, vol. 68, No. 12, Dec. 15, 1990, pp. 6526–6528.
Lateral Dopant Profiling with 200 nm Resolution by Scanning Capacitance Microscopy, C. C. Williams et al, Applied Physics Letters, vol. 65, No. 16, Oct. 16, 1989, pp. 1662–1664.

Primary Examiner—Jack B. Harvey
Assistant Examiner—Maura K. Regan
Attorney, Agent, or Firm—Price, Gess & Ubell

[57] ABSTRACT

A method and apparatus of determining the amount of impurities in an object with isothermal capacitance transient spectroscopy (ICTS) includes maintaining the object at a constant temperature while applying a predetermined voltage pulse to the object at predetermined test locations. The capacitance is measured over a predetermined time period, and the measured capacitance is processed to determine the amount of impurities in accordance with a differential coefficient obtained by differentiating the following equation used as the ICTS spectrum:

$$K(t) = \int_o^{t/2} C^2(t')\,dt' - \int_{t/2}^t C^2(t')\,dt'$$

wherein C is the capacitance and t is the time period.

8 Claims, 5 Drawing Sheets

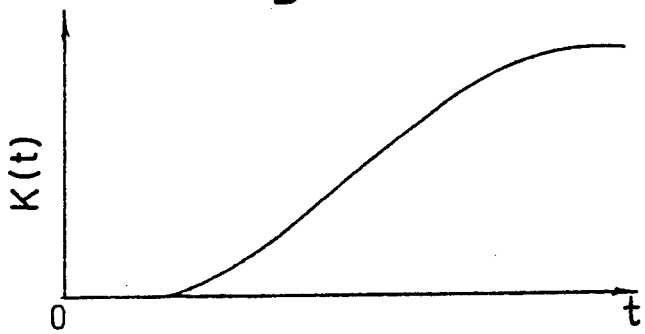
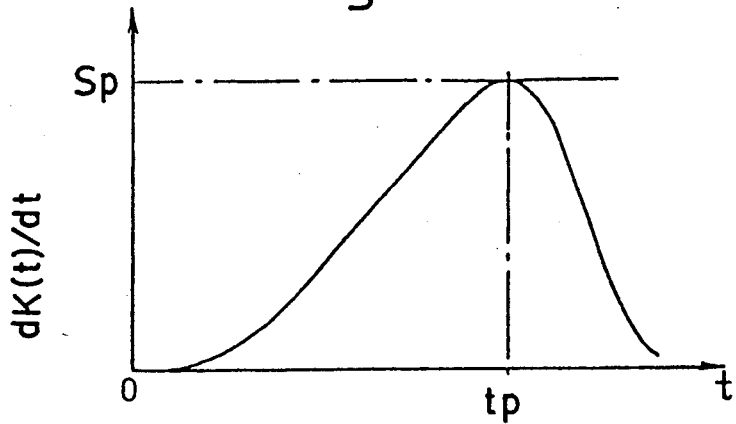

ISOTHERMAL CAPACITANCE TRANSIENT SPECTROSCOPY METHOD AND APPARATUS

BACKGROUND OF THE INVENTION

1. Field of the Invention

The present invention relates to a method and apparatus of nondestructively measuring impurities, defects and the like in semiconductor wafers, semiconductor chips, and electronic components in a short time period.

2. Description of Related Art

Semiconductor wafers, semiconductor chips and the like have been tested by measuring the amount of impurities, defects or the like contained therein. A method of measuring such impurities contained in semiconductors by an isothermal capacitance transient spectroscopy (ICTS) procedure has been known.

Referring to FIGS. 1 and 2, reference numeral 1 designates a transient capacitance meter system provided with a pulse generator 2, a transient capacitance meter 3, and an A/D converter 4 therewithin. A constant temperature bath 5 is provided with a semiconductor sample 6, and a pair of probes 7 and 8 are connected with the transient capacitance meter 1. The probes 7 and 8 are provided with contact needles 9 and 10, respectively, with pointed ends. Reference numeral 11 designates a computer system, and reference numeral 12 designates a plotter, while reference numeral 13 designates a display screen.

In order to measure impurities contained in the semiconductor sample 6 by the use of the transient capacitance meter system 1, the respective pointed ends of the contact needles 9 and 10 are brought into spaced contact with a portion to be measured of the semiconductor sample 6, at an appointed constant temperature, as shown in FIG. 2. Under such conditions, the semiconductor sample 6 has an appointed magnitude of pulse voltage, generated by the pulse generator 2, applied to it. Subsequently, a signal based on an electrostatic capacitance in the portion to be measured of the semiconductor sample 6 is measured by the transient capacitance meter 3. The signal is subjected to an A/D conversion, followed by being operated upon by a measurement algorithm program in the computer 11, thereby measuring the impurities, defects and the like contained in the semiconductor sample 6.

However, in the conventional isothermal capacitance transient spectroscopy, the ICTS spectrum S(t) has been defined by the following equation, where a capacitance transient waveform, as shown in FIG. 5(A), is expressed by C(t), and S(t) is expressed by the following Equation (1):

$$S(t) = t \frac{dC^2(t)}{dt} \quad (1)$$

In this case, $C^2(t)$, which is the square of $C(t)$, is expressed by the following Equation (2):

$$C^2(t) = C_o^2 \left\{ 1 + \frac{N_T}{N_D} \exp\left(-\frac{t}{\tau}\right) \right\} \quad (2)$$

wherein $C_o$ designates a stationary capacitance and $N_p$ designates a concentration of impurities intentionally added.

A concentration of impurities, $N_T$, and a thermal emission time constant, $\tau$, are calculated by the following Equation (3) from a peak intensity $S_p$ of the measured ICTS spectrum and at a peak time $t_p$:

$$N_T = \frac{2.72 N_D}{C_o^2} S_p \quad (3)$$

$$\tau = t_p$$

However, in the above-described conventional isothermal capacitance transient spectroscopy, when the applied capacitance-change is small as compared with a resolving power of the capacitance meter 3 or external turbulent noises are also generated, then noises are added to the C(t). Thus S(t), which is obtained by directly differentiating the $C^2(t)$, is violently fluctuated, as shown in FIG. 5(B). As a result, the accuracy of measurement of a specific concentration of impurities, $N_T$, and the thermal emission time constant, $\tau$, have been lessened, or impurities of a relatively low concentration will not be able to be detected under such circumstances.

Thus, the prior art is still seeking to provide an improved capacitance testing procedure and apparatus for determining impurities.

SUMMARY OF THE INVENTION

It is an object of the present invention to provide an isothermal capacitance transient spectroscopy method and apparatus capable of accurately detecting impurities of low concentration, and thus achieving a highly accurate measurement.

In order to achieve the above-described object, the present invention uses isothermal capacitance transient spectroscopy, in which a pulse voltage having an appointed magnitude is applied to a semiconductor sample held at a constant temperature to analyze a subsequent capacitance-change of the semiconductor sample. The impurities are determined in the semiconductor sample by a differential coefficient obtained by differentiating an expression defined by the following Equation (4) for the ICTS spectrum:

$$K(t) = \int_o^{t/2} C^2(t') \, dt' - \int_{t/2}^t C^2(t') \, dt' \quad (4)$$

Also, a differential coefficient obtained by differentiating an expression defined by the following Equation (5) may also be used as the ICTS spectrum in place of the differential coefficient obtained by differentiating the Equation (4):

$$K(t) = \int_o^{t/2} C(t') \, dt' - \int_{t/2}^t C(t') \, dt' \quad (5)$$

In addition, a differential coefficient obtained by differentiating Equation (6) may also be used as the ICTS spectrum in place of the differential coefficient obtained by differentiating Equation (4).

$$K(t) = \int_o^{t/2} \{C(t') - C_n\}^2 dt' - \int_{t/2}^t \{C(t') - C_n\}^2 dt' \quad (6)$$

In addition, a differential coefficient obtained by differentiating Equation (7) may be used as the ICTS spectrum in place of the differential coefficient obtained by differentiating Equation (4).

$$K(t) = \int_0^{t/2} \{C(t') - C_n\}dt' - \int_{t/2}^{t} \{C(t') - C_n\}dt' \quad (7)$$

According to the present invention, in the case where, for example, Equation (4) is used, the S/N in this expression is improved, so that the ICTS spectrum is improved in S/N by 10 times or more. As a result, the accuracy of measurement of the concentration of impurities and thermal emission time constant can be improved. Thus, impurities of low concentration in the amount of 1/0 times or less, as compared with that in the conventional method, can be detected.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 3(A) is a diagram showing a capacitance transient waveform;

FIG. 3(B) is a diagram showing an integrated capacitance transient waveform;

FIG. 3(C) shows the ICTS spectrum;

DESCRIPTION OF THE PREFERRED EMBODIMENTS

Figure 1:
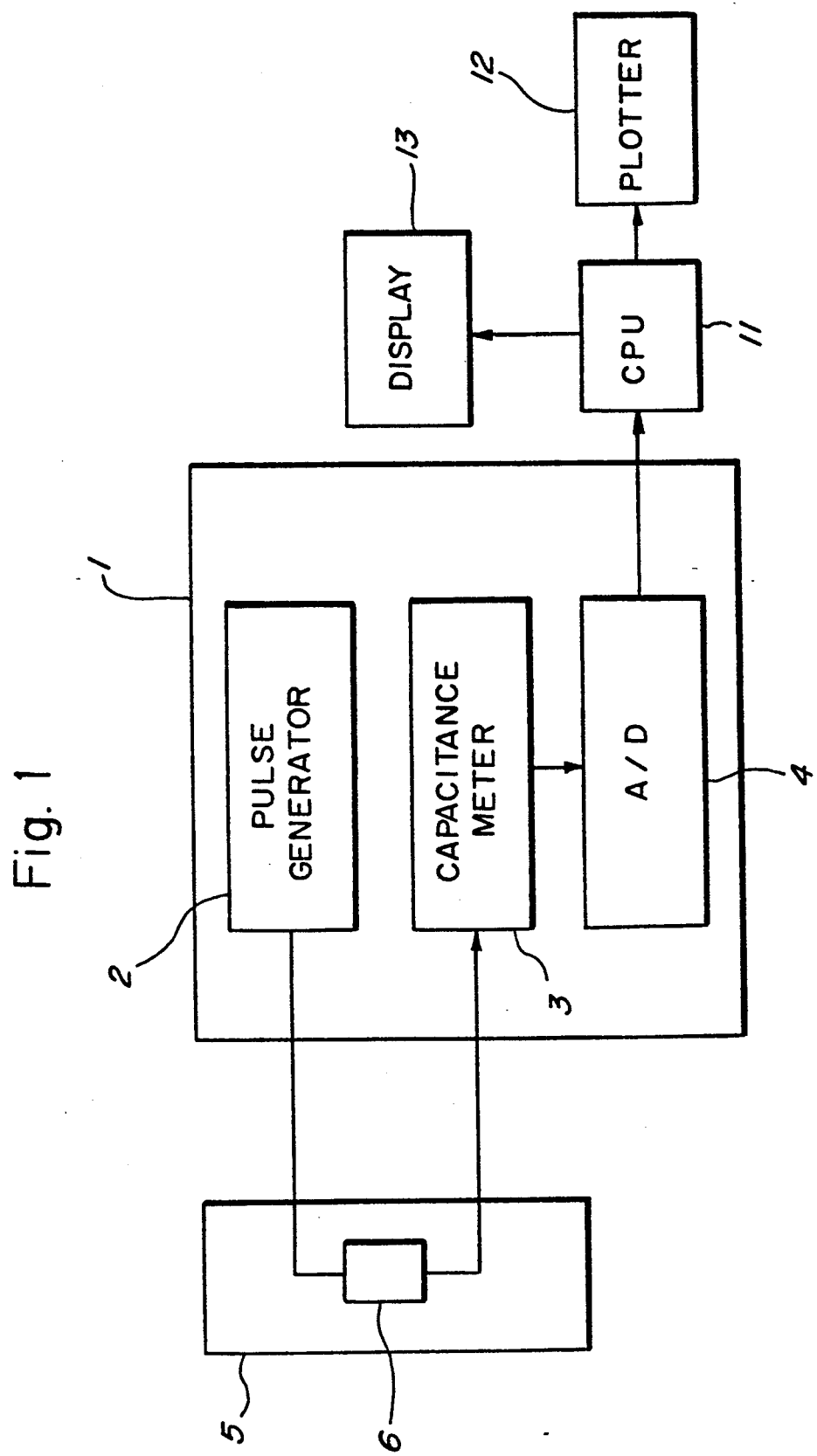
FIG. 1 is a block diagram schematically showing an apparatus for isothermal capacitance transient spectroscopy according to the present invention.
Figure 2:
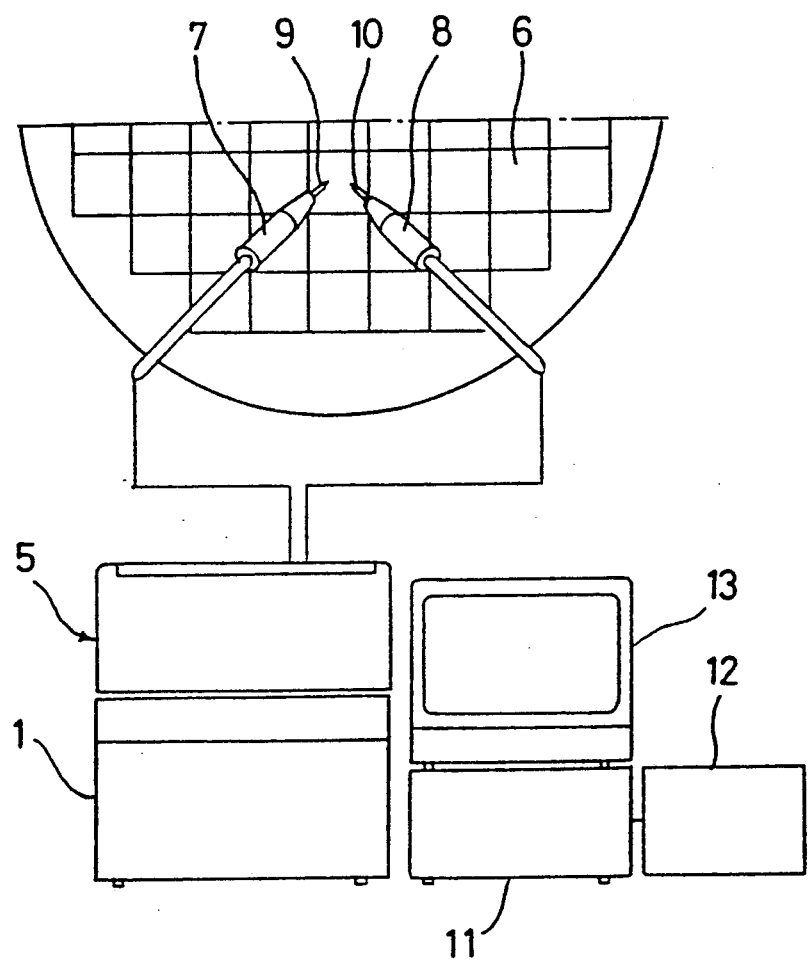
FIG. 2 is a diagram showing essential parts of the spectroscopy apparatus.

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a method and apparatus for isothermal capacitance transient spectroscopy.

The preferred embodiments of the present invention will be described below. According to a first preferred embodiment, in an isothermal capacitance transient spectroscopy, a pulse voltage having an appointed magnitude is applied to a semiconductor sample, which is held at a constant temperature, to analyze a resultant capacitance-change of the semiconductor sample. The quantity of impurities and the like contained in the semiconductor sample can be determined by an expression defined by the following Equation (4):

$$K(t) = \int_0^{t/2} C^2(t') dt' - \int_{t/2}^{t} C^2(t') dt' \quad (4)$$

A differential coefficient obtained by differentiating $K(t)$ defined by Equation (4) is used as the ICTS spectrum, and this is expressed by the following Equation (8):

$$S(t) = \frac{dK(t)}{dt} \quad (8)$$

In this case, the concentration of impurities, $N_T$, and the thermal emission time constant, $\tau$, are expressed by the following Equation (9) on the basis of Equation (2):

$$N_T = \frac{4N_D}{C_o^2} S_p \quad (9)$$

$$\tau = 0.721 t_p$$

In the above equations, the following terms are utilized:
$C_o$ = stationary capacitance
$C$ = capacitance
$t$ = time
$\tau$ = thermal emission time constant of impurities
$t_p$ = peak time
$N_T$ = unknown concentration of impurities
$N_D$ = known concentration
$S_p$ = peak intensity of ICTS spectrum Equation (9) will be further described below with reference to FIG. 3. As shown in FIG. 3(A), $C(t)$ is the actual measured sample capacitance, and it has a time dependence after the initial and predetermined bias voltage pulse is applied to the sample for a predetermined time. The term "$C_o$" is the equilibrium capacitance established in the sample after the application of the bias voltage pulse. Provided that a capacitance transient waveform $C(t)$ is as shown in FIG. 3(A), the $K(t)$ obtained according to Equation (4) (that is, an integrated capacitance transient waveform) is as shown in FIG. 3(B). As understood from FIG. 3(B), the integrated capacitance transient waveform $K(t)$ is improved in S/N. This $K(t)$ is differentiated to use the obtained differential coefficient as the ICTS spectrum. This ICTS spectrum has a waveform as shown in FIG. 3(C) and is improved in S/N 10 times or more, as compared with the above-described conventional method. Accordingly, an accuracy of measurement of the concentration of impurities and thermal emission time constant can be improved. Thus, impurities of low concentration 1/10 times or less, as compared with that in the conventional method, can be detected.

The present invention is not limited by the above-described first preferred embodiment. A differential coefficient obtained by differentiating an expression defined by the following Equation (5) may also be used as the ICTS spectrum:

$$K(t) = \int_0^{t/2} C(t') dt' - \int_{t/2}^{t} C(t') dt' \quad (5)$$

A concentration of unknown impurities, $N_T$, and a thermal emission time constant, $\tau$, in this second preferred embodiment are expressed by the following Equation (10):

$$N_T = \frac{8N_D}{C_o} S_p \quad (10)$$

$$\tau = 0.721 t_p$$

In this second preferred embodiment, an expression which is approximate as compared with that in the above-described first preferred embodiment is used, so that the accuracy is slightly inferior, but the expression is comparatively simple. Thus, an advantage occurs in that the calculation can also be conducted, if desired, by an analog circuit.

Figure 4:
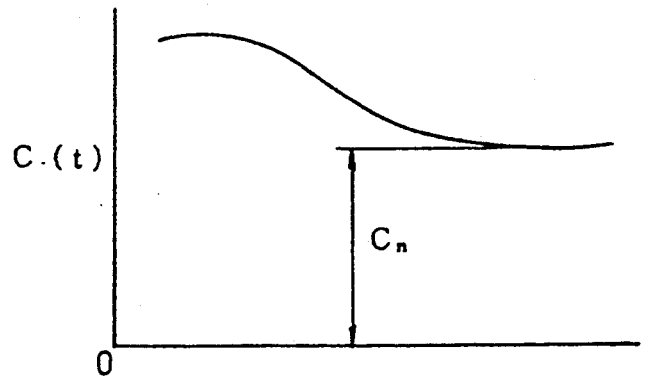
FIG. 4 is a diagram for describing an invariable fraction $C_n$.
Figure 5A:
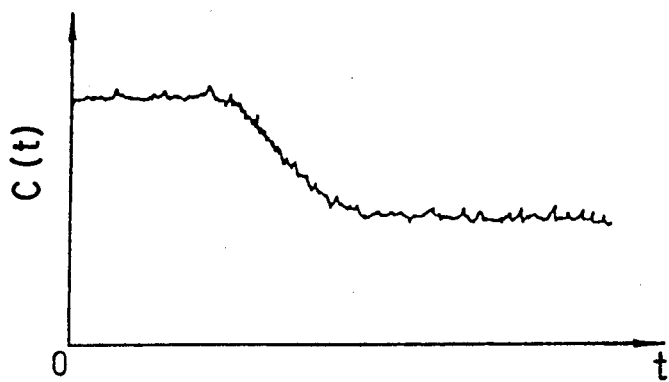
FIG. 5(A) is a diagram showing a capacitance transient waveform.
Figure 5B:
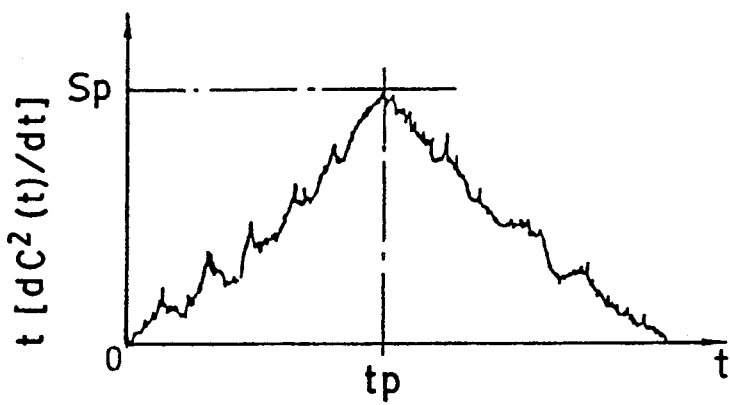
FIG. 5(B) shows the ICTS spectrum.

In addition, in the case where the capacitance transient waveform C(t) includes an invariable fraction, $C_n$, as shown in FIG. 4, the following Equation (6) may be used as K(t) in the above-described first and second preferred embodiments. $C_n$ is the nullbalance capacitance, which can be determined either manually by the operator from a display screen, or can be determined automatically by the computer system. If a capacitance meter directly measures C(t), then a relatively larger capacitance range (e.g. 1,000 pf) must be used. If the capacitance meter measures $C(t) - C_n$, then a small capacitance range (e.g. 100 pf) can be used. Generally, the smaller capacitance range has a higher capacitance resolution capability so that $C_n$ is important in enabling such resolution.

Thus, a differential coefficient obtained by differentiating Equation (6) may be used as the ICTS spectrum.

$$K(t) = \int_0^{t/2} \{C(t') - C_n\}^2 dt' - \int_{t/2}^t \{C(t') - C_n\}^2 dt' \quad (6)$$

A concentration of impurities, $N_T$, and a thermal emission constant, $\tau$, in this third preferred embodiment are expressed by the following Equation (11):

$$N_T = \frac{4N_D}{C_o(C_o - C_n)} S_p \quad (11)$$

$$\tau = 0.721 t_p$$

In this third preferred embodiment, an effective number of figures in a signal processing operation by the computer is increased, so that there is the possibility that the accuracy of the calculation is improved.

In addition, a differential coefficient obtained by differentiating an expression defined by the following Equation (7) may be used as the ICTS spectrum:

$$K(t) = \int_0^{t/2} \{C(t') - C_n\} dt' - \int_{t/2}^t \{C(t') - C_n\} dt' \quad (7)$$

A concentration of impurities, $N_T$, and a thermal emission time constant, $\tau$, in this fourth preferred embodiment are expressed by the following Equation (12):

$$N_T = \frac{8N_D}{C_o} S_p \quad (12)$$

$$\tau = 0.721 t_p$$

In this fourth preferred embodiment, an expression which is approximate as compared with that in the above-described third preferred embodiment is used, so that the accuracy is slightly inferior, but the expression is comparatively simple. Thus, calculations can also be conducted by an analog circuit and, at the same time, an effective number of figures in an operation by the computer is increased. Thus, there is still the possibility that the accuracy of calculations can be improved.

In the preferred embodiments, a digital signal processing is performed with a computer program. The selected mathematical equation for the particular embodiment is implemented in a software algorithm program in a manner well known in the art so that the operator can prepare the sample to achieve an isothermal state by inserting it into a constant temperature bath. The sample is permitted to equalize to the environment, and probes 7 and 8 can be applied to the desired test area of the sample. A predetermined bias voltage is applied as a pulse for a set time period. The measurement time cycle is then started and the data representing C(t) is collected and then converted to binary information and stored, for example, in a register to be assigned to a RAM memory. The data can then be processed pursuant to the desired mathematical equation, depending on the particular embodiment to be implemented, to provide an output of measured impurities.

As described above, according to the present invention, the ICTS spectrum is improved in S/N 10 times or more, as compared with the conventional method. Thus, an accuracy of measurement of concentration of impurities and thermal emission time constant can be improved. Thus, impurities of low concentration 1/10 times or less, as compared with that in the conventional method, can be detected.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method of determining the amount of impurities in an object with isothermal capacitance transient spectroscopy (ICTS), comprising the steps of:
   maintaining the object at a constant temperature;
   applying a predetermined voltage pulse to the object at predetermined test locations;
   measuring the capacitance over a predetermined time period, and
   processing the measured capacitance to determine the amount of impurities in accordance with a differential coefficient obtained by differentiating the following equation used as the ICTS spectrum:

$$K(t) = \int_0^{t/2} C^2(t') dt' - \int_{t/2}^t C^2(t') dt'$$

wherein C is the capacitance and t is the time period.

2. A method of determining the amount of impurities in an object with isothermal capacitance transient spectroscopy (ICTS), comprising the steps of:
   maintaining the object at a constant temperature;
   applying a predetermined voltage pulse to the object at predetermined test locations;
   measuring the capacitance over a predetermined time period, and processing the measured capacitance to determine the amount of impurities in accordance with a differential coefficient obtained by differentiating the following equation used as the ICTS spectrum:

$$K(t) = \int_{o}^{t/2} C(t') \, dt' - \int_{t/2}^{t} C(t') \, dt'$$

wherein C is the capacitance and t is the time period.

3. A method of determining the amount of impurities in an object with isothermal capacitance transient spectroscopy (ICTS), comprising the steps of:
maintaining the object at a constant temperature;
applying a predetermined voltage pulse to the object at predetermined test locations;
measuring the capacitance over a predetermined time period, and
processing the measured capacitance to determine the amount of impurities in accordance with a differential coefficient obtained by differentiating the following equation used as the ICTS spectrum:

$$K(t) = \int_{o}^{t/2} \{C(t') - C_n\}^2 dt' - \int_{t/2}^{t} \{C(t') - C_n\}^2 dt'$$

wherein C is the capacitance and t is the time period.

4. A method of determining the amount of impurities in an object with isothermal capacitance transient spectroscopy (ICTS), comprising the steps of:
maintaining the object at a constant temperature;
applying a predetermined voltage pulse to the object at predetermined test locations;
measuring the capacitance over a predetermined time period, and
processing the measured capacitance to determine the amount of impurities in accordance with a differential coefficient obtained by differentiating the following equation used as the ICTS spectrum:

$$K(t) = \int_{o}^{t/2} \{C(t') - C_n\} dt' - \int_{t/2}^{t} \{C(t') - C_n\} dt'$$

wherein C is the capacitance and t is the time period.

5. An improved apparatus for determining the amount of impurities in an object with isothermal capacitance transient spectroscopy (ICTS), comprising:
means for maintaining the object at a constant temperature;
means for applying a predetermined voltage pulse to the object at predetermined test locations;
means for measuring the capacitance over a predetermined time period, and
means for processing the measured capacitance to determine the amount of impurities in accordance with a differential coefficient obtained by differentiating the following equation used as the ICTS spectrum:

$$K(t) = \int_{o}^{t/2} C^2(t') \, dt' - \int_{t/2}^{t} C^2(t') \, dt'$$

wherein C is the capacitance and t is the time period.

6. An improved apparatus for determining the amount of impurities in an object with isothermal capacitance transient spectroscopy (ICTS), comprising:
means for maintaining the object at a constant temperature;
means for applying a predetermined voltage pulse to the object at predetermined test locations;
means for measuring the capacitance over a predetermined time period, and
means for processing the measured capacitance to determine the amount of impurities in accordance with a differential coefficient obtained by differentiating the following equation used as the ICTS spectrum:

$$K(t) = \int_{o}^{t/2} C^2(t') \, dt' - \int_{t/2}^{t} C^2(t') \, dt'$$

wherein C is the capacitance and t is the time period.

7. An improved apparatus for determining the amount of impurities in an object with isothermal capacitance transient spectroscopy (ICTS), comprising:
means for maintaining the object at a constant temperature;
means for applying a predetermined voltage pulse to the object at predetermined test locations;
means for measuring the capacitance over a predetermined time period, and
means for processing the measured capacitance to determine the amount of impurities in accordance with a differential coefficient obtained by differentiating the following equation used as the ICTS spectrum:

$$K(t) = \int_{o}^{t/2} \{C(t') - C_n\}^2 dt' - \int_{t/2}^{t} \{C(t') - C_n\}^2 dt'$$

wherein C is the capacitance and t is the time period.

8. An improved apparatus for determining the amount of impurities in an object with isothermal capacitance transient spectroscopy (ICTS), comprising:
means for maintaining the object at a constant temperature;
means for applying a predetermined voltage pulse to the object at predetermined test locations;
means for measuring the capacitance over a predetermined time period, and
means for processing the measured capacitance to determine the amount of impurities in accordance with a differential coefficient obtained by differentiating the following equation used as the ICTS spectrum:

$$K(t) = \int_{o}^{t/2} \{C(t') - C_n\} dt' - \int_{t/2}^{t} \{C(t') - C_n\} dt'$$

wherein C is the capacitance and t is time period.

* * * * *